(12) United States Patent
Massicotte et al.

(10) Patent No.: US 7,194,298 B2
(45) Date of Patent: Mar. 20, 2007

(54) METHOD AND APPARATUS FOR TREND DETECTION IN AN ELECTROCARDIOGRAM MONITORING SIGNAL

(75) Inventors: Louis Massicotte, Québec (CA); Jean-François Montplaisir, Québec (CA)

(73) Assignee: Medicale Intelligence Inc., Québec (CA)

( * ) Notice: Subject to any disclaimer, the term of this patent is extended or adjusted under 35 U.S.C. 154(b) by 481 days.

(21) Appl. No.: 10/262,667

(22) Filed: Oct. 2, 2002

(65) Prior Publication Data

US 2004/0068196 A1 Apr. 8, 2004

(51) Int. Cl.
*A61B 5/402* (2006.01)
(52) U.S. Cl. ..................................... 600/509
(58) Field of Classification Search ........... 600/382, 600/509, 515–519, 521–523; 607/4, 5, 9, 607/30–32, 60, 62, 63
See application file for complete search history.

(56) References Cited

U.S. PATENT DOCUMENTS

| | | | | |
|---|---|---|---|---|
| 4,589,420 A | * | 5/1986 | Adams et al. | 600/515 |
| 5,113,869 A | * | 5/1992 | Nappholz et al. | 600/508 |
| 5,416,695 A | | 5/1995 | Miller et al. | |
| 6,083,248 A | * | 7/2000 | Thompson | 607/30 |
| 6,656,125 B2 | * | 12/2003 | Misczynski et al. | 600/508 |
| 2002/0042579 A1 | | 4/2002 | Rowlandon | |

\* cited by examiner

*Primary Examiner*—Robert E. Peruto
*Assistant Examiner*—Frances P. Oropeza
(74) *Attorney, Agent, or Firm*—Ogilvy Renault, LLP; Isabelle Chabot

(57) ABSTRACT

The present invention can be used in conjunction with a wearable digital wireless ECG monitoring system. A full ECG curve is received by a central module. The central module is worn on the belt like a cellular or a pager. It is made of four different devices operating together: a hand-held computer, a GPS, a cellular board and a multiplexing device. The system wirelessly receives the complete cardiac curve from the ECG and is able to distinguish not only the beat rate, but also to analyze any abnormal heart contractions. In fact, most common heart diseases are not related to the acceleration or deceleration of the heart rate. In case of problem detected by the central unit, the system automatically calls a central station and can send the GPS positioning and ECG monitoring of the patient with the detected anomaly data. Voice communication with the patient or the passers by is also possible.

22 Claims, 13 Drawing Sheets

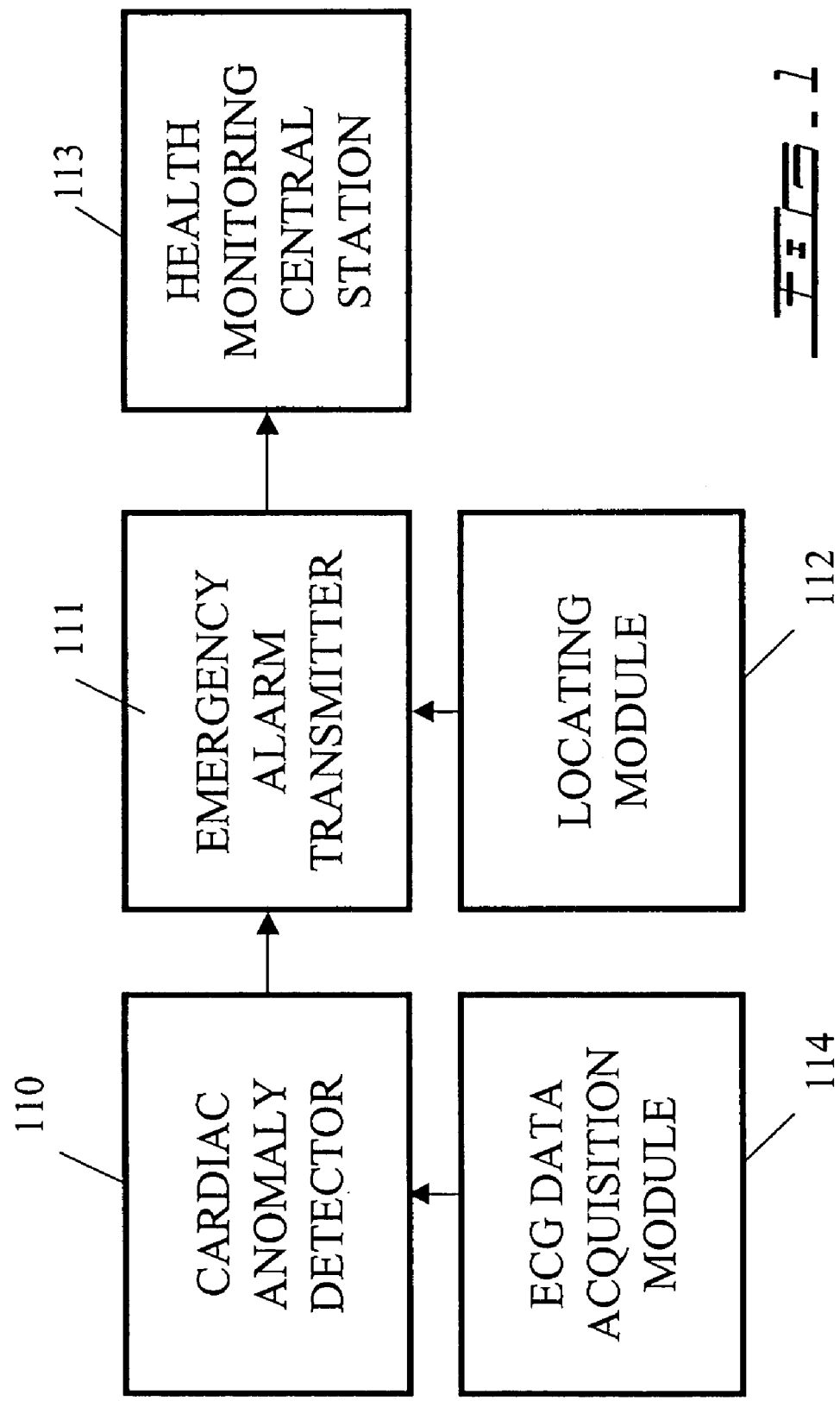

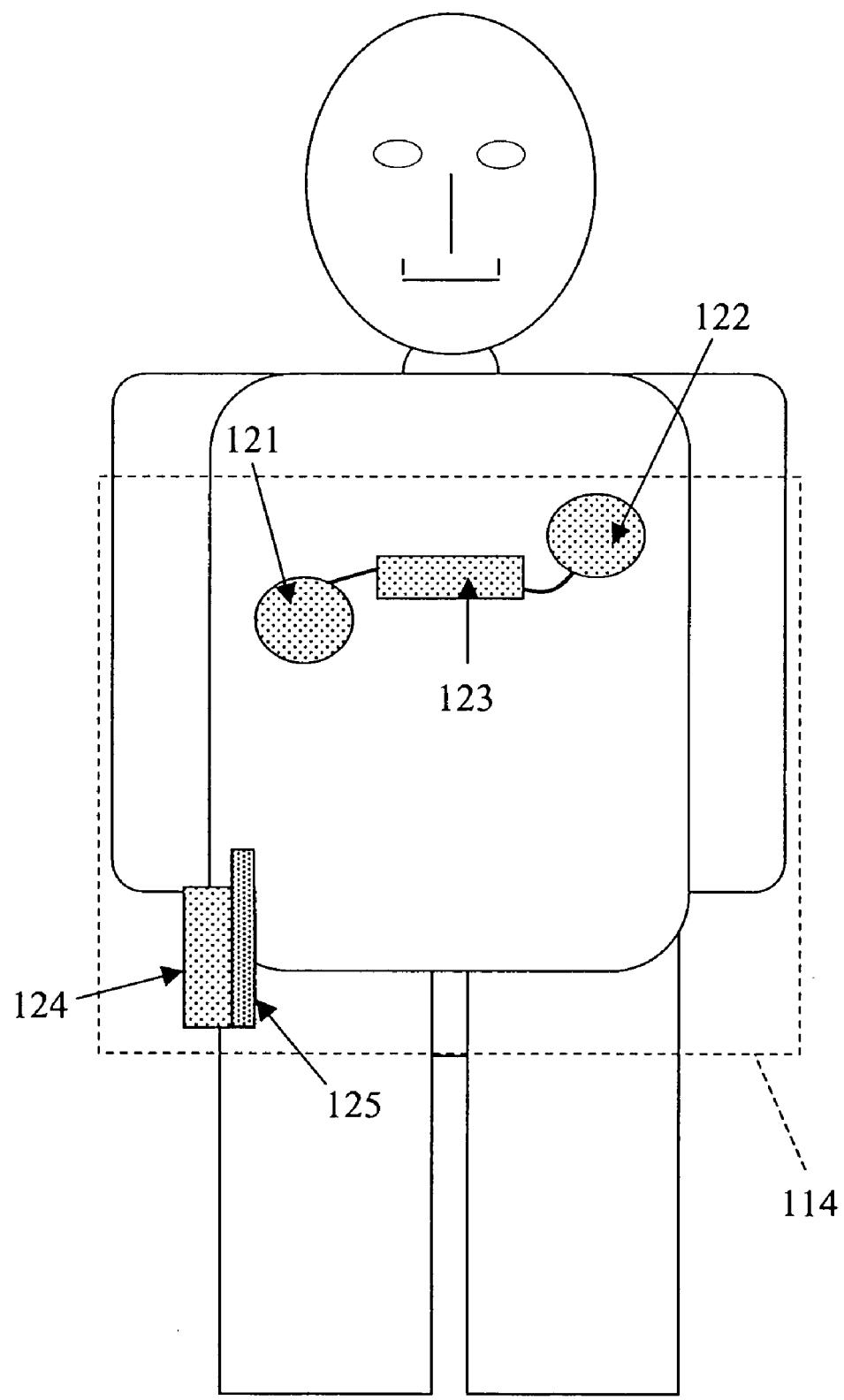

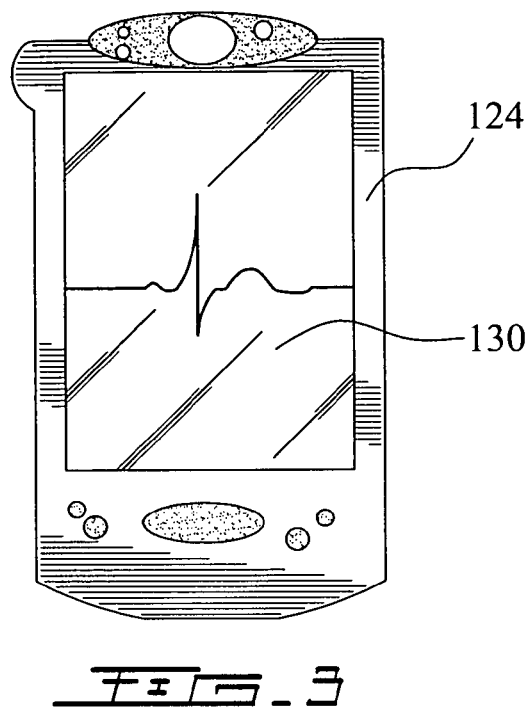
FIG_3
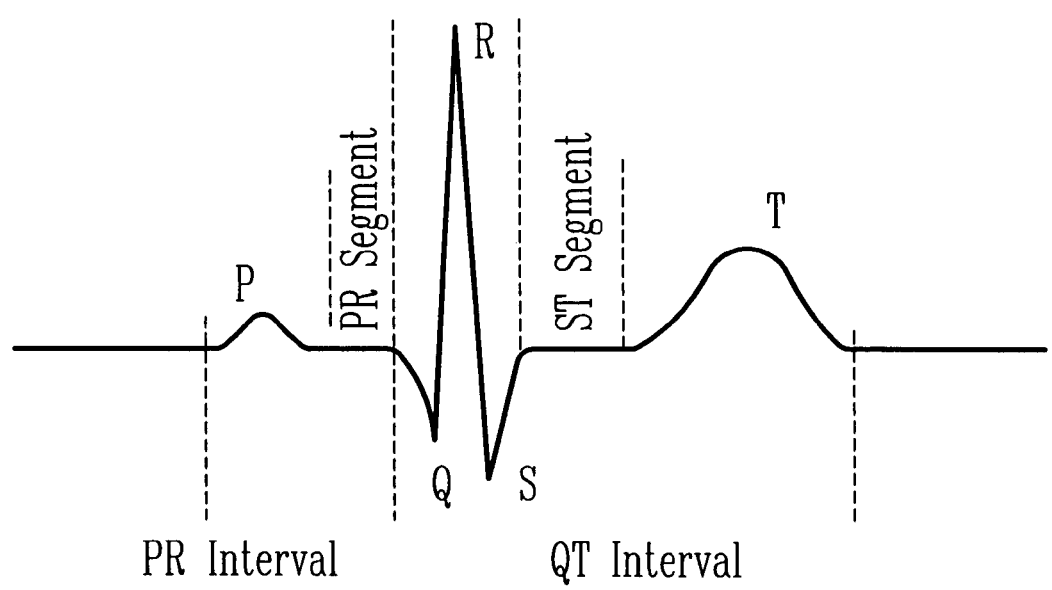
FIG_4

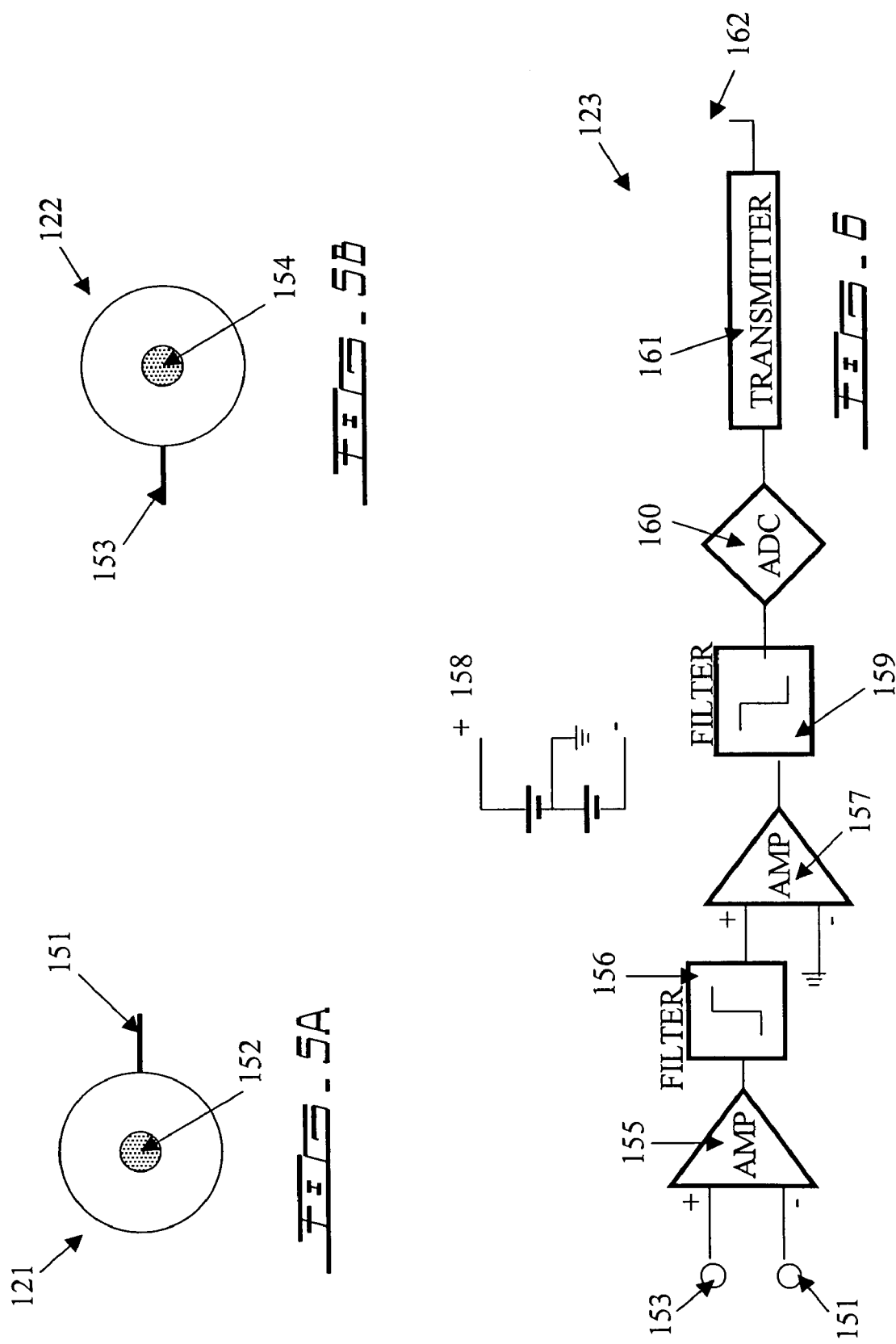

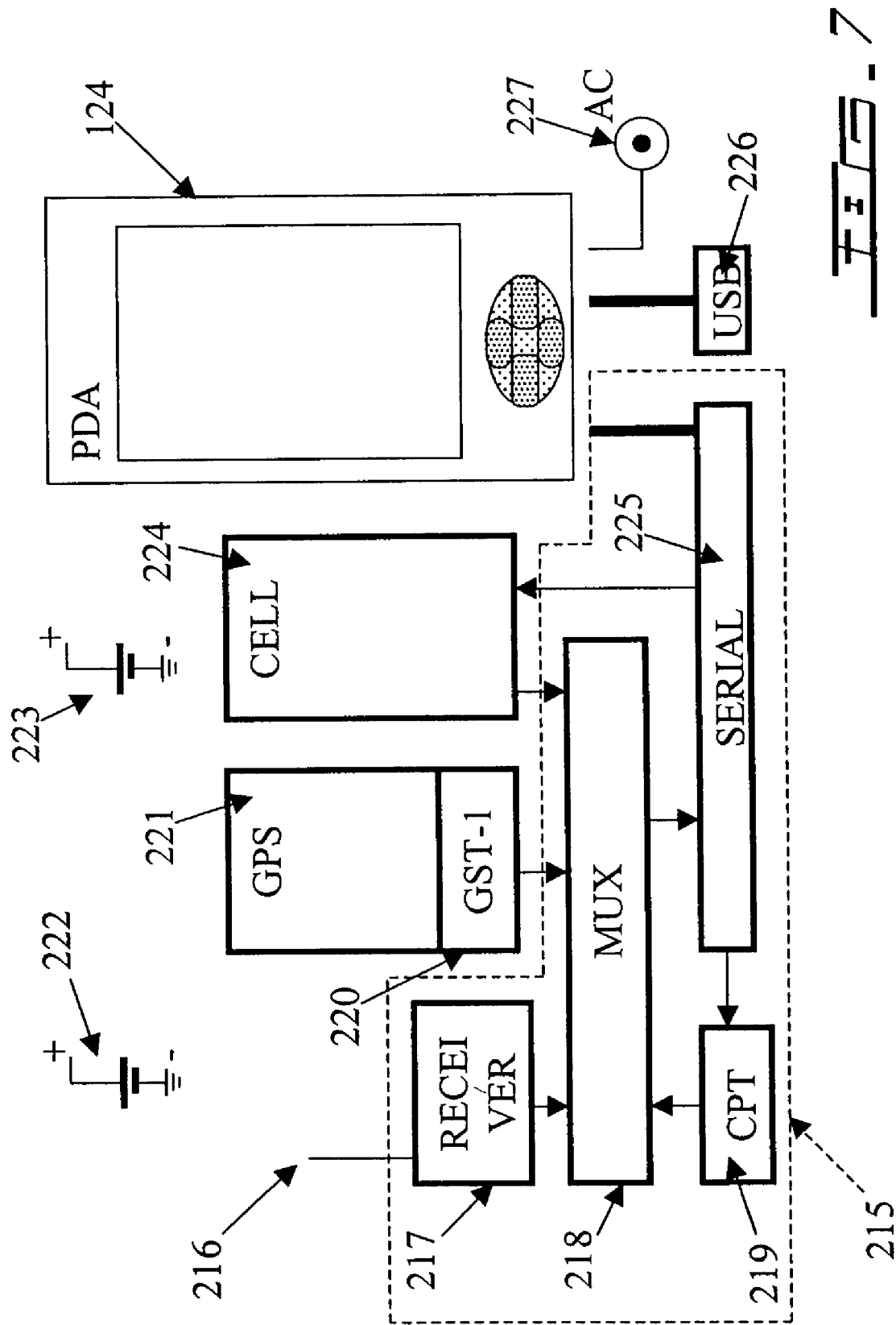

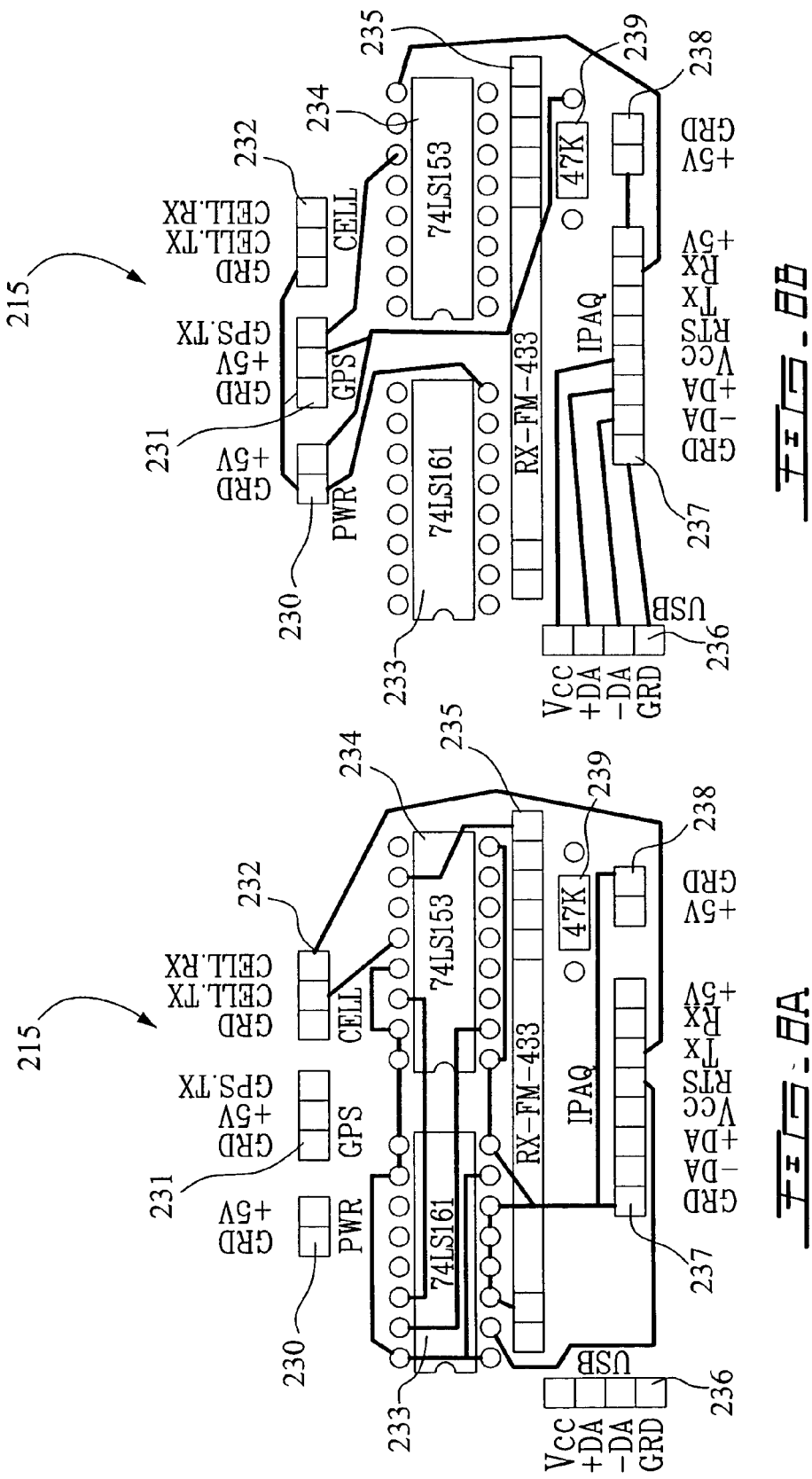

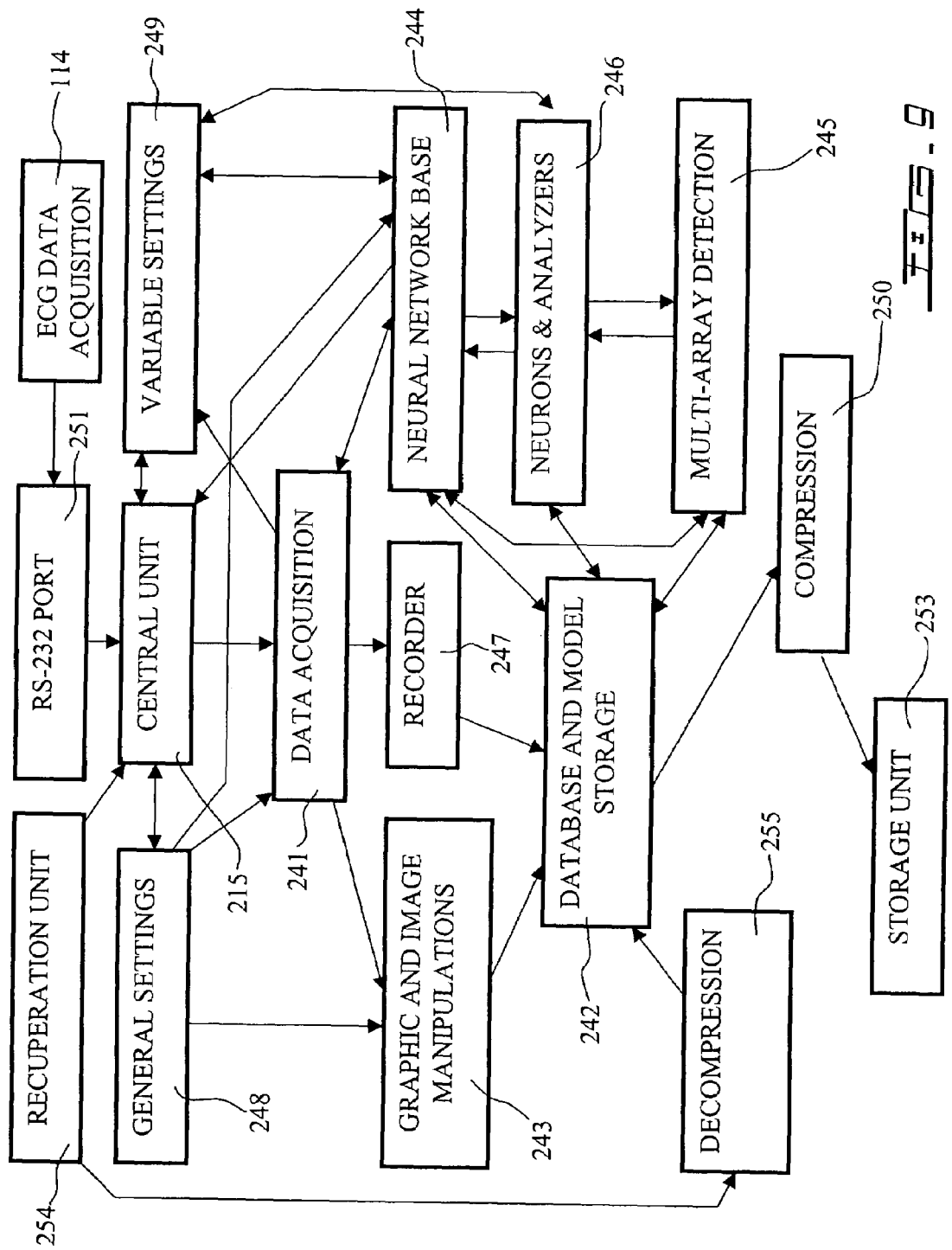

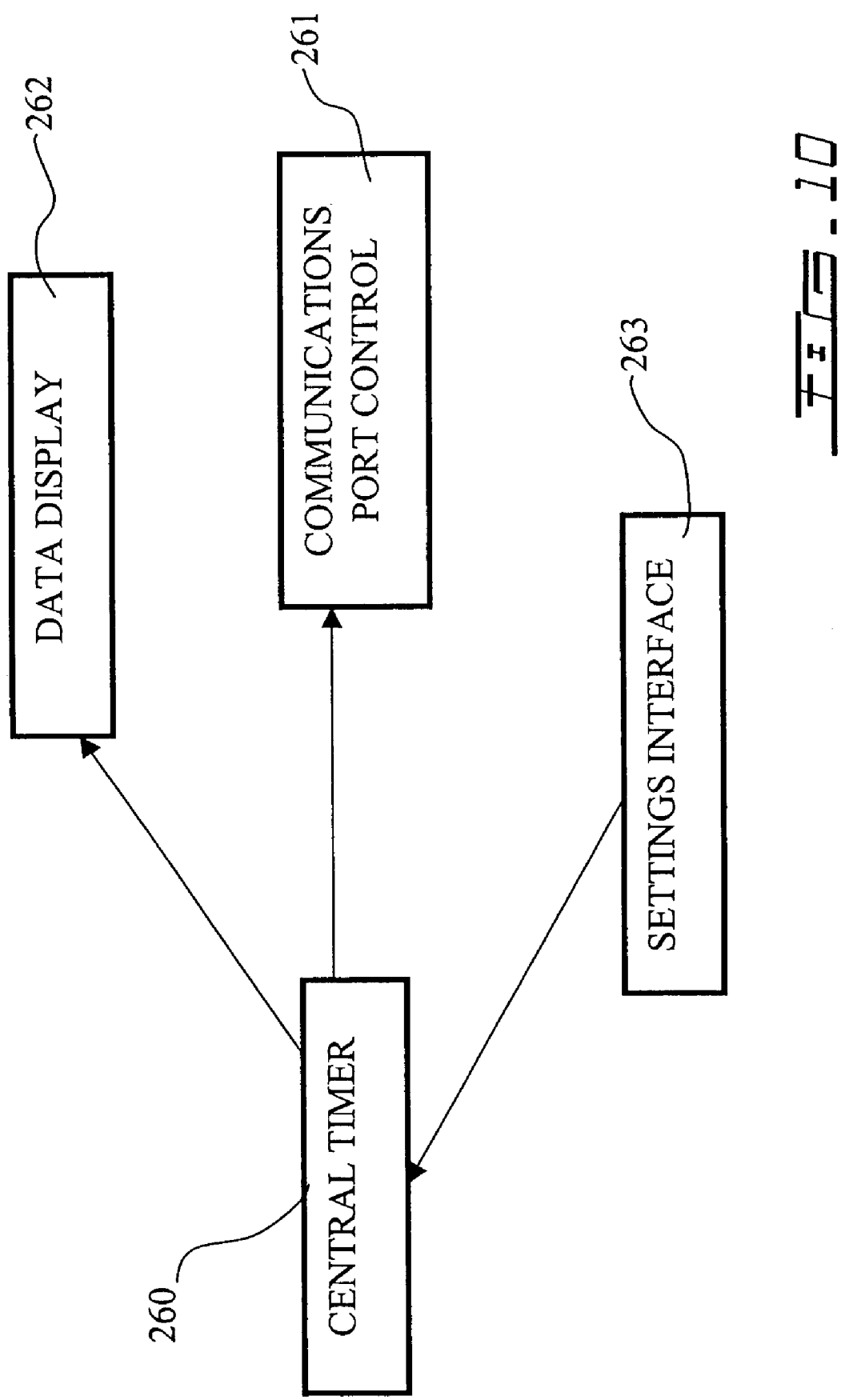

FIG_14

METHOD AND APPARATUS FOR TREND DETECTION IN AN ELECTROCARDIOGRAM MONITORING SIGNAL

FIELD OF THE INVENTION

The invention relates to monitoring and analyzing heart activity and in particular to trend detection in an electrocardiogram monitoring signal.

BACKGROUND OF THE INVENTION

Heart diseases are increasingly common in adults of all ages. Recent statistics have stated that sixty million North Americans suffer from heart disease. Because the North American society is getting older, the risk of suffering from heart diseases increases every year. People are now more aware of their health and need ways to apply preventive medicine.

An electrocardiogram (ECG/EKG) is an electrical recording of the heart that is used in the investigation of heart disease. Cardiologists have confirmed the urgent need for devices that can be worn for a long period to provide an ECG covering more than twenty-four hours. The idea is to enable the observation of cardiac events that are not regularly present in heart activity.

Cardiac contractions are the result of a well orchestrated electrical phenomenon called depolarization. Cell membranes move from their negative resting potential to a more positive threshold which ultimately stimulates them to contract. In the myocardium there are specialized fibers that are very conductive and allow the rapid transmission of electrical impulses across the muscle, telling them to contract. In order to maximize the force of the contraction there is uniformity in the sequence. That is, the atria contract, then the ventricles contract. This allows both sets to fill properly before ejecting the blood to its next destination. These two sections are independent, yet linked to a single impulse, (in a healthy heart,) initiated by the sinoatrial, (or sinus) node. The tissue around the valves helps to channel the impulse from the sinus node through another collection of specialized tissue, the atrioventricular node, that is situated between the two sets of chambers. This area allows slightly slower transmission of the impulse to the ventricles, allowing the atria to empty into the ventricles before they contract and force the blood to the lungs or body. This area, the A/V Node, slows the impulse down to about one twenty-fifth of the original signal then passes it through to the atrioventricular bundle, or the bundle of His. This bundle divides itself into two distinct tracts through the ventricles, the bundle branches, and on to the Purkinje fibers, where the muscle of the ventricle is stimulated to contract from the bottom up, maximizing the force of ejection.

An electrical current in the direction towards the positive end of a bipolar electrode causes a positive deflection of the stylus of the ECG. If the number of myocardial cells (dipoles) in this direction increases, the current will increase as well. The greater the current, the more positive the voltage. An electrical current in the direction away from the positive end of a bipolar electrode causes a negative deflection of the stylus of the ECG. If the number of myocardial cells (dipoles) in this direction increases, the current will increase as well. The greater the current, the more negative the voltage.

The ECG Library authored by Dean Jenkins and Stephen Gerred and found on the Internet at http://www.ecglibrary.com/ in September 2002 is a very good source of information on ECGs.

An article of particular interest with respect to artificial intelligence in medical devices was published by Ralph Begley et al. in March 2000 in the Medical Device & Diagnostic Industry Magazine at page 150 and is entitled "Adding Intelligence to Medical Devices". This article can be found on the Internet in September 2002 at the Medical Devicelink Site at hftp://www.devicelink.com/mddi/archive/00/03/014.html.

Most portable ECGs currently available on watches or the like can only record heartbeat. Although this is sufficient to determine if a patient is under cardiac arrest, it is insufficient to detect other cardiac anomalies, defects and diseases.

Prior art portable monitor systems are manufactured by a few companies, such as the Biolog™ portable ECG by Lyppard, the CCW-CAS Cardio Perfect CE™ resting ECG system by Cardio Control, the PocketView™ 12 Lead portable ECG system by Numed, the Portable ECG/Respiration Monitor by Harvard Apparatus and the Digital Angel™ Safety and Location Monitor, ThermAlert™ Watch and Alerts by Digital Angel Corporation. These monitoring devices allow partial collection of the patient's ECG data but do not offer full collection and analysis of the data, detection of anomalies and transmission of alarms and integration with traditional medical equipment and emergency central stations. Because of these drawbacks, they cannot be used to replace traditional Holter readings and cannot ensure the patient's safety.

SUMMARY OF THE INVENTION

An object of the present invention is to analyze complete ECG data collected to detect anomalies and report alarms.

A further object of the present invention is to monitor the ECG data for the patient at all times and request emergency assistance if required.

Another object of the present invention is to locate a patient, if he is unable to provide his location, using a positioning module, especially during emergency assistance requests.

The present invention can be used in conjunction with a wearable digital wireless ECG monitoring system. A full ECG curve is received by a central module. The central module is worn on the belt like a cellular or a pager. It is made of four different devices operating together: a hand-held computer, a GPS, a cellular board and a multiplexing device. The system wirelessly receives the complete cardiac curve from the ECG and is able to distinguish not only the beat rate, but also to analyze any abnormal heart contractions. In fact, most common heart diseases are not related to the acceleration or deceleration of the heart rate. In case of problem detected by the central unit, the system automatically calls a central station and can send the GPS positioning and ECG monitoring of the patient with the detected anomaly data. Voice communication with the patient or the passers by is also possible.

According to one broad aspect of the present invention, there is provided a trend detection method for detecting trends in an electrocardiogram monitoring signal of a patient. The method comprises extracting locations of base points from the electrocardiogram monitoring signal; determining an occurrence of a trend in the electrocardiogram monitoring signal from the locations.

According to another broad aspect of the present invention, there is provided a trend detection system for detecting trends in an electrocardiogram monitoring signal of a patient. The system comprises a base point location extractor for extracting locations of base points from the electrocardiogram monitoring signal; a trend occurrence determiner for determining an occurrence of a trend in the electrocardiogram monitoring signal from the locations.

BRIEF DESCRIPTION OF THE DRAWINGS

These and other features, aspects and advantages of the present invention will become better understood with regard to the following description and accompanying drawings wherein:

FIG. 1 is block diagram of the main components of the preferred embodiment;

FIG. 2 is a graphical representation of the wearable device of the preferred embodiment;

FIG. 3 is a graphical representation of the user interface of the computer;

FIG. 4 is a graphical representation of an ECG wave;

FIG. 5A and FIG. 5B are block diagrams of the electrodes;

FIG. 6 is a block diagram of the transformation of the electrode signal into a wireless output;

FIG. 7 is a block diagram of the components of the emergency transmitter module;

FIGS. 8A and 8B are, respectively, top and bottom views of a realization of the central unit;

FIG. 9 is a detailed block diagram of the main components of the preferred embodiment;

FIG. 10 is a block diagram of the components of the central unit;

DETAILED DESCRIPTION OF THE PREFERRED EMBODIMENT

Figure 11:
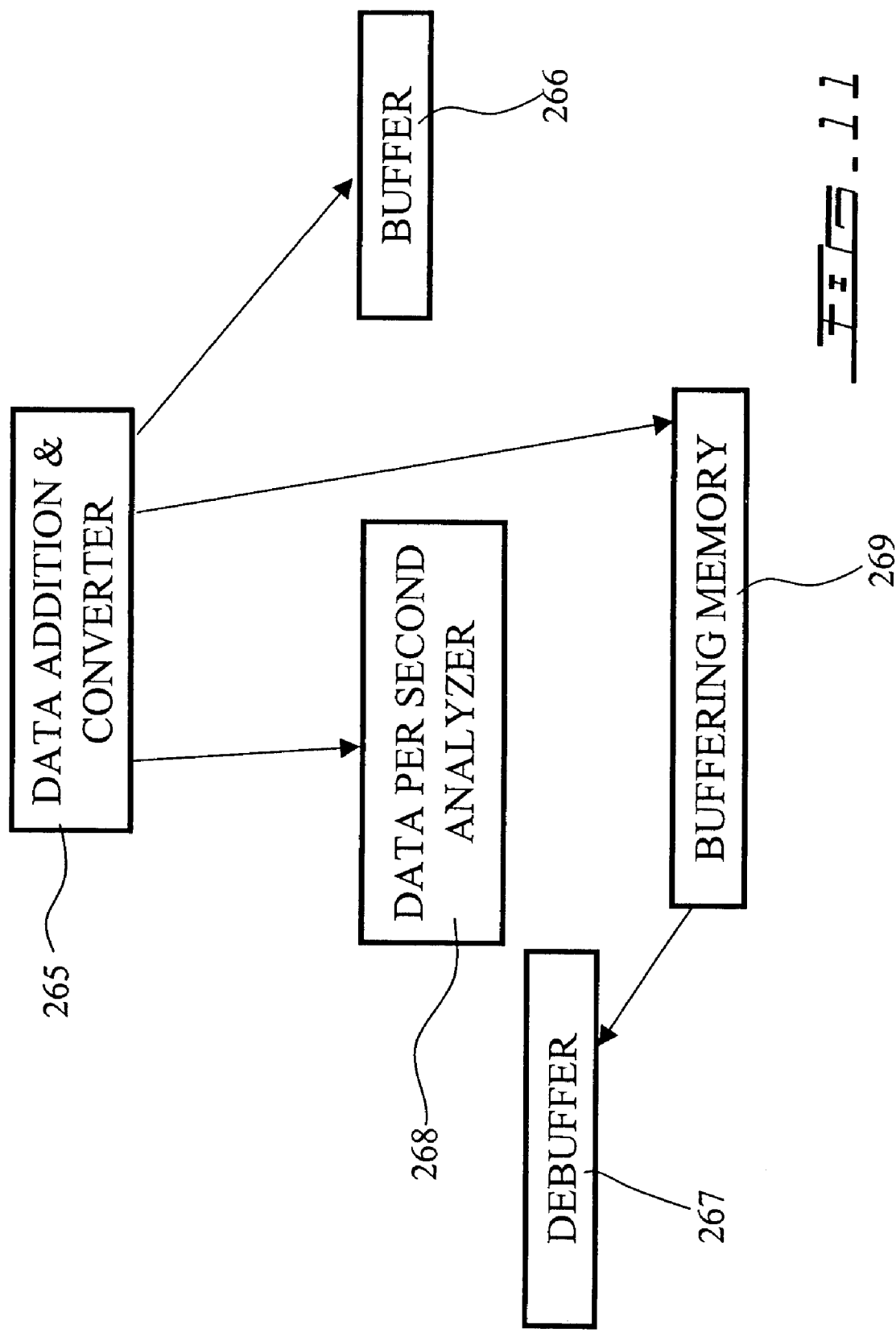
FIG. 11 is a block diagram of the components of the data acquisition module.

While illustrated in the block diagrams as groups of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment.

The present invention is for a personal emergency alarm system. With reference to FIG. 1, it comprises five main components: a full ECG monitoring device 114 which collects the ECG data from the patient and transmits it to a cardiac anomaly detector 110 which detects anomalies in the ECG data, a locating module 112 which can use a GPS module to locate the position of the patient wearing the personal emergency alarm system, a transmitter 111 for transmitting an emergency alarm when an anomaly is detected and which can include the position of the patient, and a health monitoring central station 113 which receives the emergency alarm and dispatches appropriate help to the location of the patient.

The ECG data acquisition module 114 is preferably a full wireless ECG system which ensures that the patient can attend his day-to-day activities without being held back by the wires of the electrodes.

With reference to FIG. 2, the ECG data acquisition module 114 preferably comprises two electrodes 121 and 122 which are applied to the body of the patient and which perform data acquisition to produce a differential signal. The acquired data is then processed in an electrode signal processor 123 which performs digital sampling and digital modulation and sends the acquired data on Radio Frequency (RF). The digital sampling is done to reduce noise from interferences and magnetic fields. The distance traveled by the low voltage of the heart to the electrodes is reduced thereby creating a more precise curve of the heart activity. The portable ECG monitor is fully described in Applicants' co-pending U.S. patent application Ser. No. 10/262,662 filed simultaneously on Oct. 02, 2002, the specification of which is hereby incorporated by reference.

The ECG system also comprises a data receiver 125 which is a wireless portable device which can be worn on the patient's belt, in his pocket or even in a bag that he is carrying. The data receiver 125 can be connected to a computer 124, a hand-held PC, a PALM™ Pilot, a cellular or any other device which is compatible with the RS-232 protocol. The acquired data can then be displayed (see FIG. 3) on a small matrix screen of the data receiver 125 and/or on the screen 130 of the computer 124. A plurality of filters are used on the acquired data to enhance the clarity of the ECG curve obtained and to extract precise information on the patient's heart.

In general, the heart beats at regularly irregular intervals. This means that variations of frequencies of beats can be recorded, but always in a regular context of growth or decrease. Thus, a person making a physical exercise will see her pulse increase as muscular and pulmonary exercise intensifies. On the other hand, this growth will not trigger an irregularity of the cardiac beat.

The collection of the normal heart signals and the analysis of these are made via diagrammatic layouts and algorithms allowing the isolation of certain parts of the cardiac beat. With numerical filters, the various curves are distinguished from the total cardiac movement. With this type of data, it is possible to check the amplitude and the constancy of the various parts of the beat. This type of analysis makes it possible to determine, from the data, the number of beats per minute, for example.

A typical graphical representation of an ECG wave is shown at FIG. 4. Even if the ECG wave can be represented by the QRS curve and that we can deduce mathematical algorithms controlling this QRS curve, the curve will vary from one patient to the other and from one reading of a patient to another reading of the same patient. The ECG measures heart activity as follows: the P-Wave represents the electrical impulse across the atria to the A/V Node; the QRS represents the electrical impulse as it travels across the ventricles; and the T-Wave represents the electrical repolarization of the ventricles.

The QRS interval represents the time it takes for depolarization of the ventricles. Normal depolarization requires normal function of the right and left bundle branches. The QRS duration may vary with the size of the heart and is longer in the base-apex lead. A block in either the right or left bundle branch delays depolarization of the ventricle supplied by the blocked bundle, resulting in a prolonged QRS duration.

The PR interval is the time in seconds from the beginning of the P wave to the beginning of the QRS complex. It corresponds to the time lag from the onset of atrial depolarization to the onset of ventricular depolarization. This time lag allows atrial systole to occur, filling the ventricles before ventricular systole. Most of the delay occurs in the AV node. The PR interval is longer with high vagal tone. A prolonged PR interval corresponds to impaired AV conduction.

The QT interval begins at the onset of the QRS complex and terminates at the end of the T wave. It represents the time of ventricular depolarization and repolarization. It is useful as a measure of repolarization and is influenced by electrolyte balance, drugs, and ischemia. The QT interval is inversely related to heart rate. A QT interval corrected for heart rate can be calculated.

The Cardiac Anomaly Detector 110 uses the base points of the ECG curve to calculate distances, relative positions, etc. For example, the P, Q, R, S and T base points can be identified by the Cardiac Anomaly Detector 110 to further detect the anomalies or trends in the data.

Once this analysis made, the data can be compared with normal curves and can be weighted for the individual patient in an automatic way. The captured data will then allow a series of tests to be performed which can bring to the detection of cardiac problems.

Referring now to FIGS. 5A and 5B, sockets 152 and 154 of electrodes 121 and 122 are preferably each connected to a RedDot™ diaphoretic monitoring electrode manufactured by 3M. This electrode is commonly used in hospitals. Each electrode has two functions: first to intercept the electrical signal produced by the heart and second to attach the electrode to the patient's body. To ensure an adequate signal, the right electrode 121 is preferably placed beneath the right breast and the left electrode 122 is preferably placed above the left breast as is shown in FIG. 2. Wires 151 and 153 are used to connect the electrodes 121, 122 to the electrode signal processor 123.

FIG. 6 shows the steps needed to produce a wireless output of the electrodes signal. The output of the electrodes is connected via wires 151 and 153 to the inputs of the electrode signal processor 123. The right electrode is connected to the ground and to the reference pin of the amplifier and the left electrode is connected to the negative input of the amplifier. The differential signal then goes through a low-power instrumentation amplifier 155. This instrumentation amplifier provides good high gain and low noise amplification of the electrode differential signal. This amplifier eliminates the noise signal produced by the line sector. The noise commonly produced by the line sector (60 Hz) that interferes with the ECG signal (0.5 Hz to 150 Hz) is reduced by the fact that this noise appears on the positive and the negative inputs of the instrumentation amplifier. So the difference between the two inputs subtracts the noise from the ECG signal. The voltage difference between the two electrodes is filtered to a high pass filter 156 with a cut frequency of 0.5 Hz. This filter also eliminates the DC signal present on the ECG reading.

A second amplification 157 of the signal provides a total amplification ratio of 1000 (1 v/1 mv), improving the ratio between the heart signal and the noise signal. Then the heart signal is fed to a low pass filter 159 to eliminate frequencies above 150 Hz. The output signal produced by the two amplifiers and filtered between 0.5 Hz and 150 Hz is fed to an analog-to-digital converter 160 which outputs an 8-bit serial signal. The format of the signal is RS-232 compatible. The signal is then modulated to a digital FM transmitter 161. The output signal of the transmitter is fed to an antenna 162 for RF radiation. The entire circuit is powered by batteries 158 which produce a power feed between −5 volts and 5 volts.

The signal from the transmitter antenna 162 is intercepted by the receiver antenna 216 of the central unit 215 as shown in FIG. 7, and fed to a digital FM receiver 217. This receiver 217 exactly reproduces the signal from the converter 160. The RS-232 compatible signal passes through a 4:1 multiplexing device 218. The purpose of this stage is to multiplex other serial devices such as the GPS module 221, the GST-1 module 220 and the cellular phone module 224 on the same port. Device selection is made via, the RS-232 RTS pin. Each state change of the RTS line acts like a clock for the counters 219 and the value of these counters results in a RS-232 line selector. When the proper line selector is set, the receiver outputs the digital signal via the serial port 225. This signal can be processed by software via a PC, Portable PC or handheld PC 124, for example, an IPAQ™ by Compaq. The computer 124 preferably has a USB port 226 and an AC power supply 227. Power sources 222 and 223 are provided in the central unit. The voltages of these power supplies depend on the type of device used in conjunction with the invention. They are typically 3 or 5 V. For the IPAQ, a 5V supply is used. The USB port 226 is used for synchronization of the portable computer 124. The AC power supply 227 is used to charge the module and the portable computer 124.

The Multiplexer module 218 is a grouping of microcontrollers and multiplexers allowing the relay between the various modules of the system. It acts in a dependent way to a principal controller who is, preferably, the portable computer module 124. It allows the simple port communication of several sources which would normally require several ports of communication. The request via lines of orders allows to access the various modules necessary to the integration of the system. It is independent of the bandwidth of the various components.

The preferred locating module 112 is a GPS module 221 manufactured by DeLorme according to Rockwell standards. To simplify the translation of the Rockwell signals, a GST-1 module 220 by Byosystems is added allowing to seize a signal encrypted using Rockwell 9600 bps and to obtain a standard NMEA format at 4800 bps.

The Cellular Module 224 comprises a cellular modem module GPRS/CDMA/GSM from Motorola. The preferred connection is 14.4 kbps. The addition of the multiplexing module 218 allows the connection and the conservation of this connection even if the cellular is not the object chosen by the multiplexer. Therefore, there is a ghost opening of the port of the cellular 224 even if one does not want to listen to the cellular.

The Portable Computer Module 124 is optional. It allows to access and consult the data collected. The preferred modules are Ipaq™ by Compaq and Palm™ VII by 3Com.

The design of the central unit 215 of FIG. 7 preferably comprises the following parts as shown in FIGS. 8A and 8B: a SILRX-433-F FM receiver 235, a 74LS153 Multiplexer 234, a Four bits synchronous 74LS161 counter 233, a 47K resistor 239 and connections to an IPAQ™ handheld computer 237, to a Motorola GPRS cellular board 232, to a DeLorme Earthmate GPS 231 231 and to a Bionics Rockwell GST-1 translator. The Bionics Rockwell GST-1 translator is connected directly to the DeLorme Earthmate. Connections to the USB 236 and to the power supply 238 and 230 are also provided.

At any time, the portable computer module 124 can question the multiplexer module 218 to obtain the cardiac data from the receiver 217 and the GPS data from the GPS module 221. The software analysis and the data storage are made in real time. The software does data compression based on diagrams of repetitions. At the time a cardiac event is detected, the software in the computer 124 triggers the call 111 to the digital emergency station 113 via the various modules.

FIG. 9 is a detailed block diagram of the main hardware and software components of the cardiac anomaly detector 110. The first module to be detailed is the central unit 215. Preferred modules of the central unit 215 are shown in FIG. 10. The main timer unit 260 collects the data from the RS-232 port 251 through the communications port control 261. A recuperation unit 254 can be used to retrieve the data to display on the data display 262. The recuperation unit is a binary decoder for recuperation of stored data. A decompression module 255 is used to decompress the data from the recuperation unit 254 prior to storage 242. The settings interface 263 is used to access the model and neural network settings.

The data from the RS-232 port 251 is provided by the central unit 215 to a portion of the data acquisition module 241 called the data per second analyzer 268. The data acquisition module 241 is detailed in FIG. 11. The data from the central unit 215 is first provided to the data addition and converter 265 which controls the data acquisition module 241 and is then forwarded to the data per second analyzer 268. Then, the data is added to the buffering memory 269 by the buffering module 266. All these actions follow the general settings 248 used to determine data similarities. The buffering memory 269 stores the data in bytes and preserves the size of the buffer memory until the debuffer 267 asks for data from the buffering memory 269. At this point, if the buffer 266 allows the creation of an array, which means that the buffer 266 has enough data stored to be able to add at least the amount of data for an array set in the general settings 248, the data is sent to be analyzed by the Neural Network Base 244 by the data acquisition module 241. The data per second analyzer 268 evaluates how much data was sent in the last second (to be as accurate as possible) and stores it in the variable settings memory 249. The recorder 247 permits to record a portion of the session data for future consultation. The Graphic and Image Manipulations module 243 manages the screen interface to allow the use to see the collected data.

Figure 12:
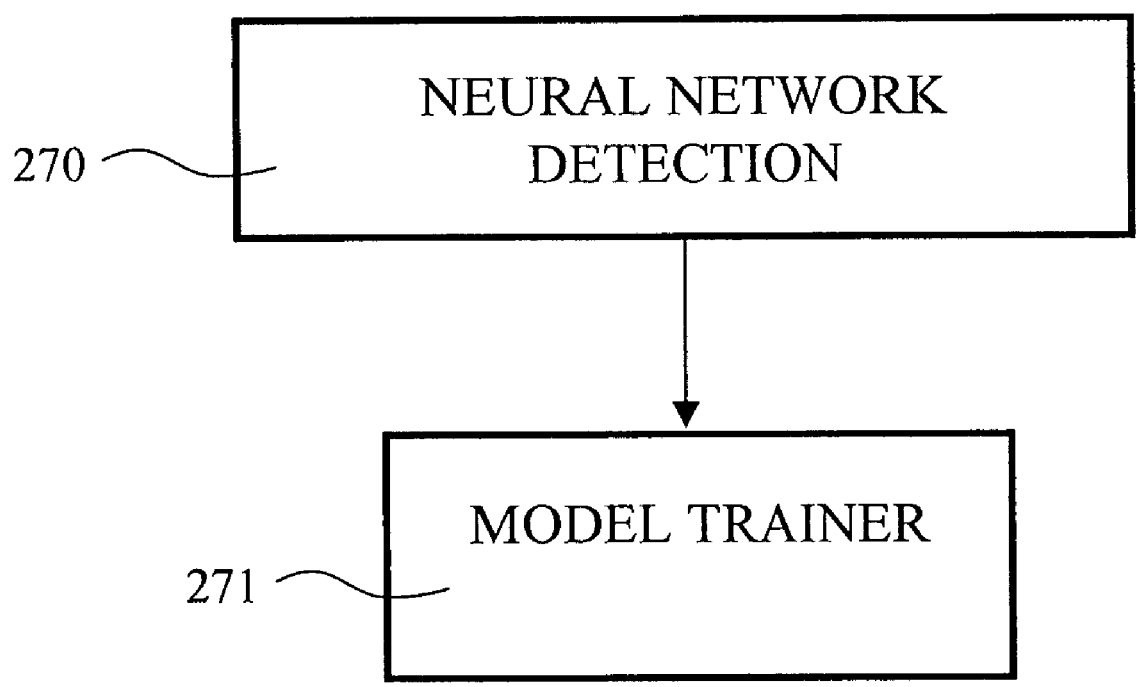
FIG. 12 is a block diagram of the components of the neural network base.
Figure 13:
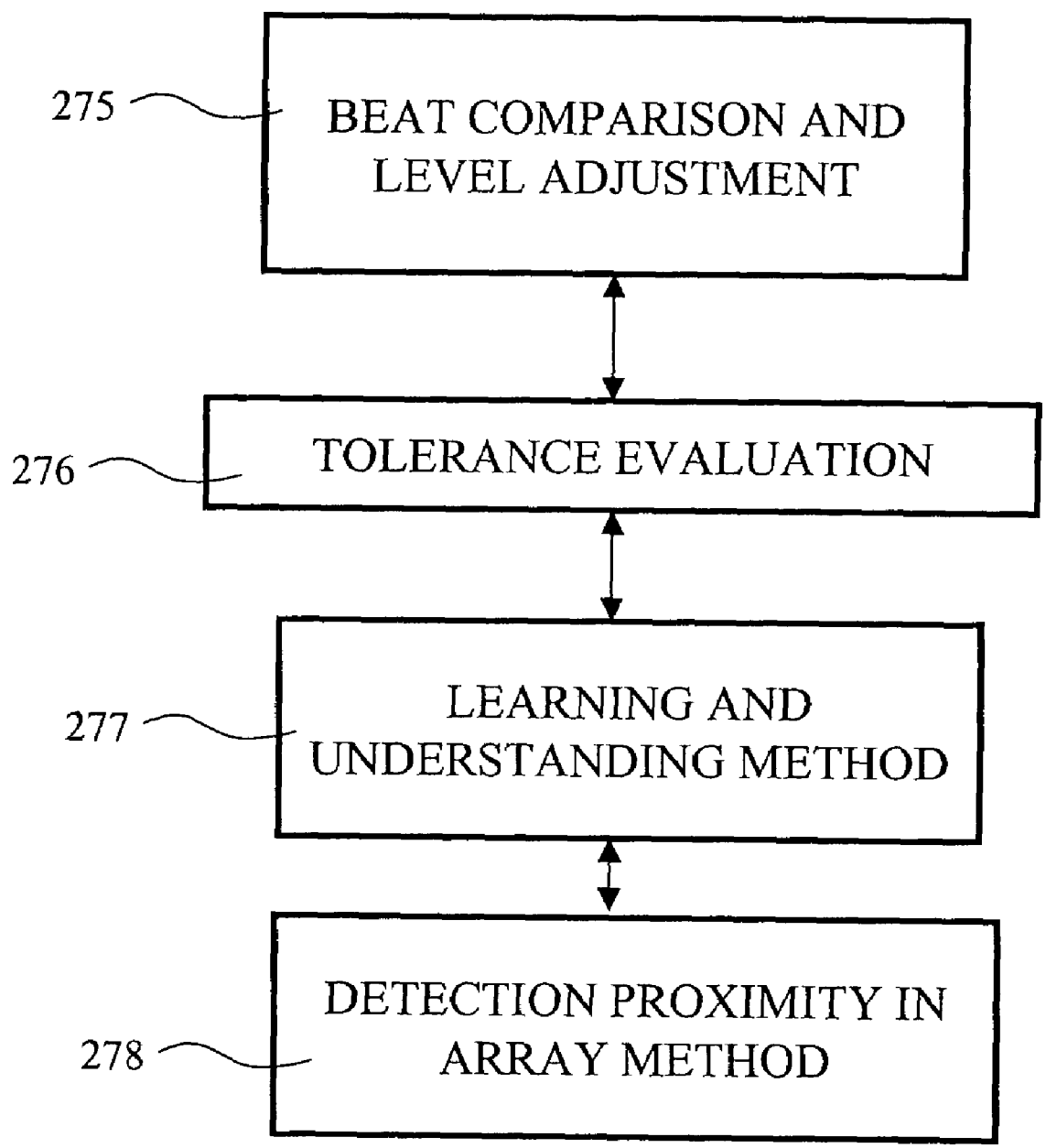
FIG. 13 is a block diagram of the components of the neurons and analyzers module.
Figure 15:
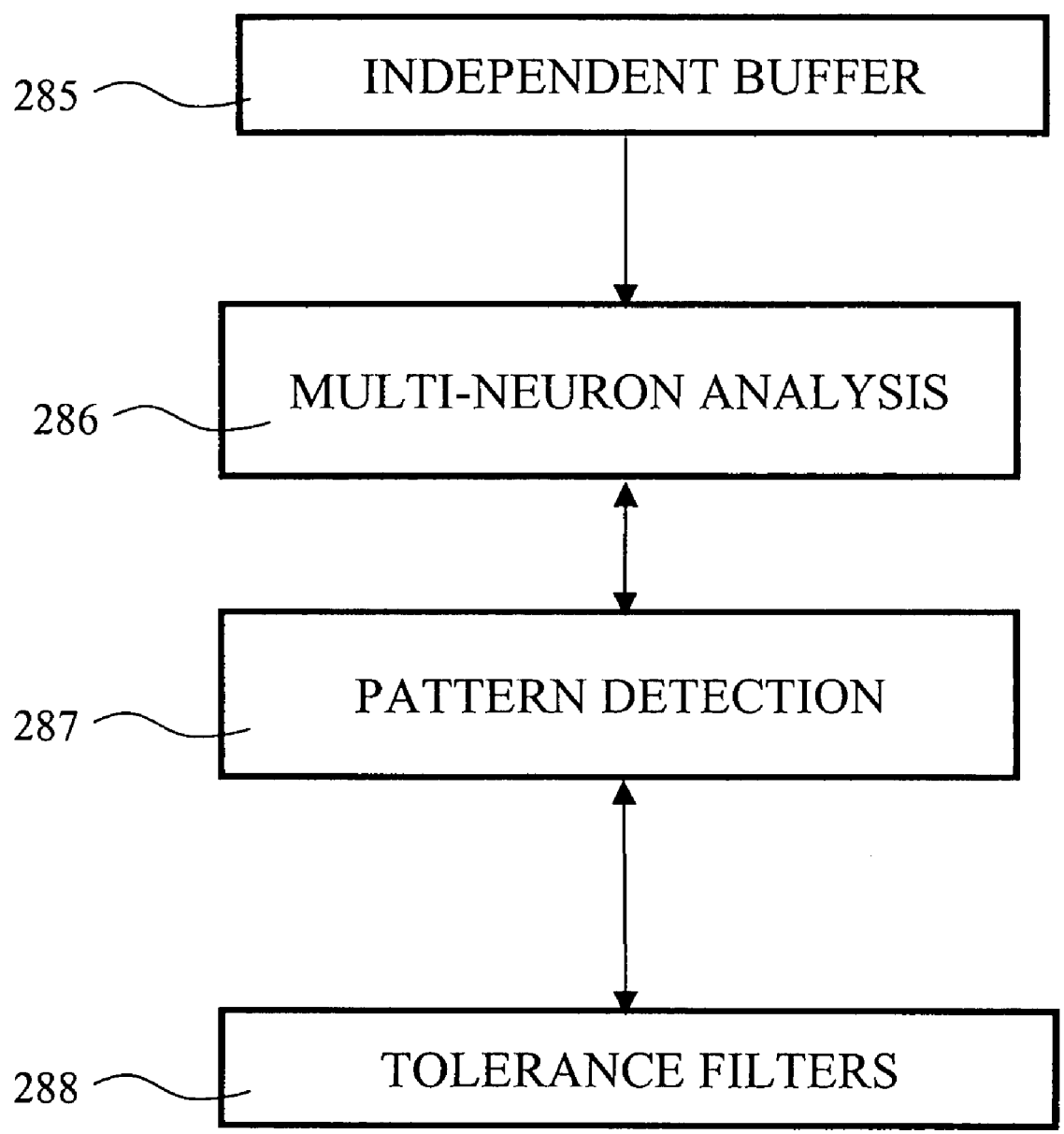
FIG. 15 is a block diagram of the components of the multi-array detection module.

The Neural Network Base 244 takes the data, array by array, and sends it to different neurons and analyzers 246 (see FIG. 12 and FIG. 15) which are able to detect many different similarities between the array and a model array stored in the database and the models 242. Using a model trainer 271, this database 242 can be adapted or improved using a simple training method. After a basic detection 270 of simple models that can detect base points of the curve such as QRS, the presence of EMG or other simple patterns, the results are sent to the multi-array detection 245 which is actually a greater analyzer that can use data sent by neurons 246 and send it to independent buffer 285 (see FIG. 19) that can be used to give a perspective on more than one array. Using this technique, it is possible to detect many more patterns that take seconds or minutes in heart activity. With tolerance filters 288 that can actually be trained to understand various heart diseases, it is possible to detect a number of problems such as arrhythmia or sinus bradicardia. The multi-neuron analyzer 286 puts in perspective as many arrays as it needs to understand a general view of the curve. This is also the best way to take a heart rate. But to ensure that the artificial intelligence is able to detect all heartbeats, a numerical filter is also provided that can extract heartbeats even in a full EMG context using a beat comparison and level adjustment module 275 (see FIG. 13). This filter, based on a Discrete Cosine Transform (DCT) algorithm, extracts parts of the result and evaluates frequency patterns 287 to evaluate the possibility of heartbeat. A digital filter is used to very precisely isolate the 70 to 90 hertz frequency range, which is the location of the main QRS peek. This kind of isolation allows detection of the heartbeat even when muscle activity is very intense.

The main use of the neurons is tolerance evaluation 276. Based on the fact that the computer needs a minimum percentage of comparisons to accept a pattern, the different neurons are requested to update the tolerance evaluation 276 to be able to detect trained models. The automatic adaptation is part of the resulting analysis. The computer is able to determine, after a very short training period (2 minutes), what should be modified to upgrade model efficiency. The learning and understanding method 277 allows to train many models in a very short time. To begin with, all trend detection systems are based on a fuzzy logic concept. The method of the present invention allows to determine a value as a function of an interval. This method, instead of only allowing the increase of the barriers of the fuzzy logic model, takes into account four more factors which can be modified during training. The array size factor can be adjusted when the neural network detects that the size of the array is too great or too small. The possibility factor allows to eliminate the improbable redundancy from the data. For example, if we know that a QRS cannot repeat itself more than 400 times per second, the neural network can automatically do negative learning if it detects that there are more than one QRS per one eighth second. The Efficiency factor is a success probability ratio based on a training done in a laboratory and allowing the neural network to know its confidence in a detected trend. Therefore, the patterns which are more often detected get a better confidence value and are then favored for the global detection process. The global tolerance is used to ensure that the model is not too evasive. Therefore, if an array is 90 percent similar to an actual model or if there is a difference between the actual model and the array greater than 3%, the neural network will choose to lower the global tolerance instead of destroying the model. This method also allows to negatively train the neural network. Therefore, if some models are detected and they should not be, the global tolerance level is increased to eliminate them from the potential choices.

The current value, the leveled adapted value and the frequency evaluation are used to compare different types of models and determine which one is right. By using more than one neuron, the difference between two very close patterns can be detected.

The detection proximity in array module 278 takes the data from both the array and the model and tries to fit them the best way it can to increase not every single piece of data but one out of ten or out of twenty without any loss of information. This technique uses an algorithm called array comparison in which the two arrays are compared point-to-point and adjusted to each other to find the very closest position possible where the two curves are similar.

Figure 14:
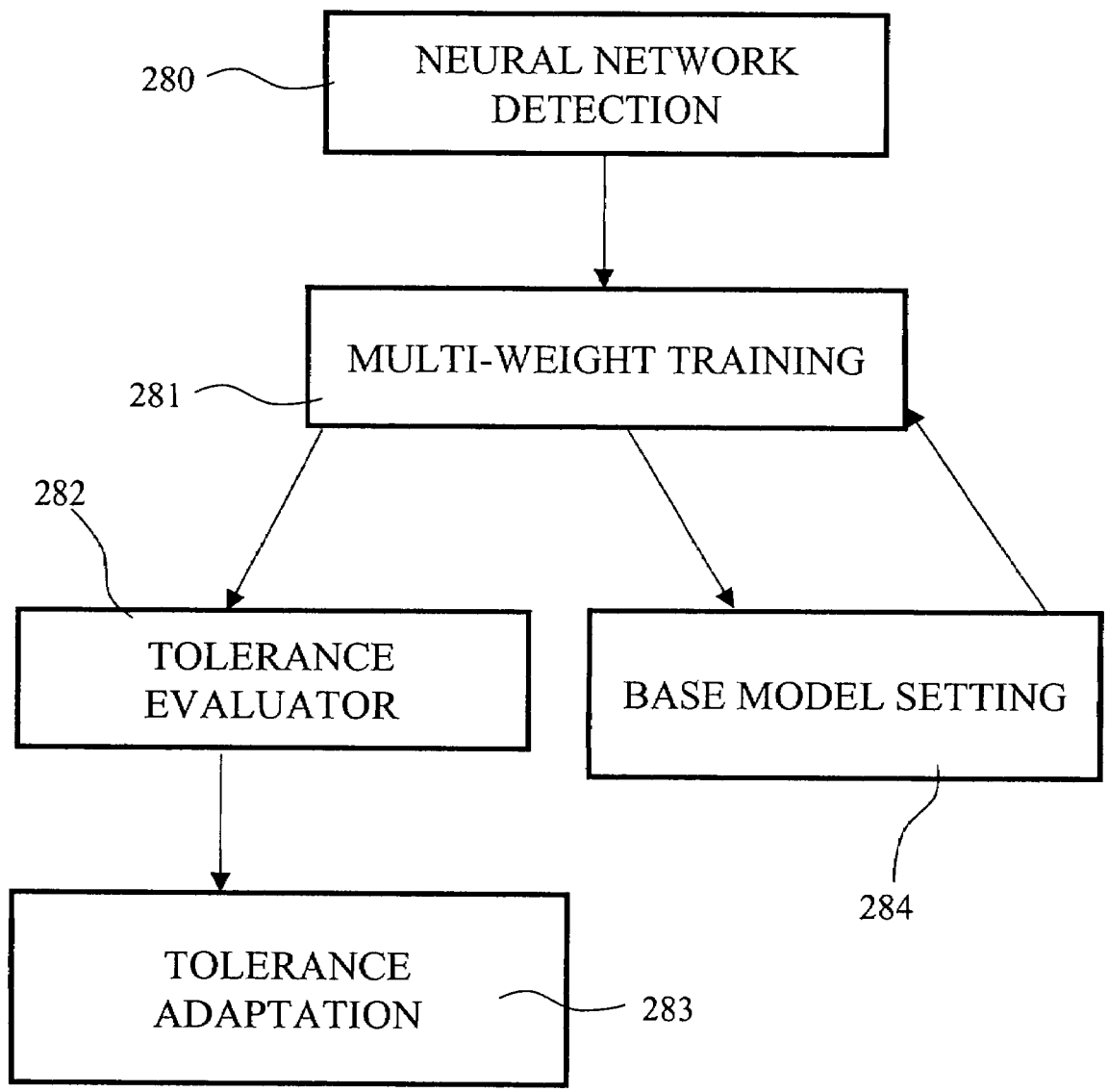
FIG. 14 is a block diagram of the components of the model trainer.

The neural network detection 280 is used to set the model database 242. Setting and training this base should be very precise. The database 242 is constructed so that it can be trained positively or negatively. The model trainer is detailed in FIG. 14. By using different weights and setting them automatically in the training session by multi-weight training 281, many more patterns can be detected. The tolerance evaluator 282 and tolerance adaptation 283 are functions that allow the least possible movement in the data to ensure the closest model possible. The Base model setting 284 allows to interface with the settings for the base models like the standard or non-standard QRS data.

In order to build the model database 242, seven neurons are preferably used. These neurons depend on each other and are hierarchically structured. The further in the decision process a neuron is, the more it depends on the inferior neurons. These neurons are connected to simple modules which manage the display, the communications and the data entry means.

The neurons and analyzers 246 will now be described in detail. The NN_detection function is as follows. A Boolean variable is assigned a false value and will be used as a key throughout the neuron functions. A buffer of 100 bytes is then created in memory using a destack function. Then, for each active model, a horizontal and vertical adjustment is done using the central positioning neuron. For each point in the array, the location of the point is compared against an upper and lower threshold value for both its horizontal and vertical adjusted values. If all points are within the predetermined threshold range, a proximity analysis is performed using a repetition verification neuron. At this point, the proximity of the last model is verified using adaptive models of the probable and improbable distances and the value is adjusted automatically. In the case where all values are valid, the Boolean key is triggered and the detection of a model value can be done. Using this technique, it is possible to order the models in a possible detection order. In fact, the neural network can ask the NN_detection to validate a possible detection in the next few arrays of 100 data. Using this technique, if one knows that a QRS has just been detected, one can ask the NN_detection to put a bigger emphasis on a T instead of trying to find another QRS right away. This technique can also be used to be more accurate and more alarmist in the detection of a cardiac arrest by giving this trend the priority.

At this point, two strings are created. These are similivectors. The data are standardized into models. Therefore, as soon as a trend is detected, instead of transferring the data into each neuron, a string containing the type of model and the time of apparition is forwarded. An example of such a string is: Q,23,R,20,S,18,T,32,B,800. This particular string would mean that a Q curve was first detected, followed by a S curve at 23 ms, etc. These curve portions and their base points are standard whatever the type of anomaly detected. For example, if a extra ventricular systole is detected, the system will first see it as a QRS followed by a T. Using such strings allows to preserve the perfect sampling and to continue the detection of the spaces and the beats per second. The second string is a string containing the detected anomalies. The detected anomalies or improbable models are stored and placed in a string in case a neuron would request them. This string is similar to the first string but also contains the definitions of the problematic models. A noise detector is also provided and will be explained shortly.

The CompareBeat function is used to center the data. Because the resolution of the data is 8 bits, and the nominal values of the electrical activities of the heart are often different, a differential and comparative function is used to find the point in the array to compare which is the closest to the model. Therefore, it is possible to increment the verification by ten points instead of verifying each data point. After having verified the chain of one hundred data points from data point one, the next data point analyzed can be data point eleven for the next chain of one hundred data points. A first calculation of the vertical space between each next point of the chain is done. Then, a scanning at intervals of four data points is done to determine the vertical position. A further scanning of all data points is done to determine the peaks and center the data points horizontally. This function returns a memory structure comprising the vertical adjustment, the horizontal adjustment and the weights of the new model structure. This is preferably not a neural function.

The DCTNoise reduction and eliminator function works as follows. Because the transmission of the electrode data is wireless, the receiver can sometimes pick up noise. Since this noise is mainly random, it is possible that some noise patterns may be similar to stored models. This function is used to determine if noise is present or not. It is used to digitally isolate frequencies. Using a discrete cosine transform algorithm to separate the data according to their frequencies, it is possible to determine the presence of a frequency typically absent in cardiac curves. Knowing that the useful frequencies in a cardiac curve are of the order of 0.0001 Hertz to 150 Hertz, this algorithm is used to eliminate all frequencies greater than 15% more than the typical range. This algorithm would be implemented as follows:

$$dctmat(u) = sum(x=0 \ldots arraysize, arraydata(x) * \cos(u*pi*(2*x+1)/(2*arraysize))).$$

Wherein u is the frequency that is looked for according to the following equation $$hertzage = int(arraysize * frequency/1000).$$

Since the DC element of the curve is eliminated earlier on, the DCT algorithm shown above does not take into account the cu variable which varies from 1 to 1/sqrt(2). The CU variable is an adapted value for the continuous input signal of the dctmat(0). Since this continuous signal is filtered in the ECG and digitally removed in the DCT, there is no need to use the CU variable typically used in common DCT algorithms. The only case where CU is different from one is when u equals 0 and this frequency is eliminate.

The output of this function is a frequency value instead of a scalar value like the input. It is then possible to detect whether high frequencies are too present. In order to do so, a learning trend based on the positioning of a median line is used and allows the computer to locate a position where there is noise or not. Therefore, by providing it with a noise baseline, a curve with reasonable noise and a curve without noise, the system is able to determine practically what constitutes noise.

This function is often used in the arrhythmia pattern detection or in the cardiac arrest pattern detection. When noise can create a temporary lack of detection of a nominal or differential value, or when the noise prevents the matching with a known model, the computer will use this function to, first, validate the presence of noise and, second, isolate the first frequencies of the standard QRS, namely 70 to 90 Hz. Therefore, even if noisy situations, or in cases of extreme muscular activity, it is possible to isolate the cardiac beat and eliminate the false arrhythmia and cardiac arrest alarms.

The multi-array detection 245 comprises many functions which will be described further. The heart rate function detects the cardiac rhythm based on the typical model type detection string. By analyzing the distances between the curves, it is possible to calculate the interval between two beats. For most cardiac sicknesses, it is important to determine the distance between the p, q, r, s and t curves and the distance between the current and next occurrences of any of these curves. Therefore, an update of these distances is always stored in the strings to ensure that the beat is synchronized. For example, there must not be an occurrence of the P curve after the QRS. Using these strings, it is clearly possible to determine the cardiac beat. For example, is the Q to Q distance is 800 samples, or 996 ms, the cardiac rhythm must be close to 60 beats per second.

However, when noise is present, the model type detection string becomes useless. It is then necessary to use the DCTNoise function. Even if it is less precise, it still allows to determine a general idea for the cardiac activity.

The Cardiac Arrest Function determines if there is a total lack of detection of the QRS, standard or not, in the model type detection string. After fifteen seconds without a QRS reading, the system determines that the patient is under cardiac arrest. When there is noise, the DCTNoise function is used to prevent false alarms.

The arrhythmia neuron is used to detect arrhythmia. Arrhythmia is a desynchronization of the heart, typically due to a lack of beats. In other words, it is an irregularity in the beats event if the configuration of the beats is regular. The arrhythmia detection algorithm detects two aspects, first, the lack of beat during a period of two seconds or more and, second, an anomaly in the distances between the QRS series. Therefore, if the distances between the QRS are not regular, the arrhythmia is detected. The normal distances between the QRS curves are learned for each patient using models and a training for the patient. In other words, if, after the detection of five or six earthman episodes, it is determined that the normal distances between the curves for this patient should be long in order to prevent false alarms, the system will adjust the parameters and will adapt to the new parameters.

The model type neuron learns from model types. It analyzes the data and creates or adapts models associated with a base model. Therefore, this neuron can be trained to detect a desynchronization of the sequence of the beat. By letting it know that the normal sequence is P, q, r, s, t, it will be able to detect an anomaly and report on it. It is also used to detect the problems with the inappropriate distances between the components of the curve. This function is typically only called when no other anomaly is detected. Therefore, if an extra ventricular systole is detected, the model type neuron will not be called to prevent multiple detections of the same problem. Distance tolerance and order analysis functions are used.

The problematic model neuron is created to detect a continuity in the anomalies. For example, even though it is abnormal for a patient to suffer from arrhythmia, it is not sufficient for this patient to have been detected with arrhythmia once in the thirty days of testing to conclude that the patient has arrhythmia. This function therefore stores the occurrences of anomalies throughout the test period to take a global look at the anomalies detected. For example, an excitement in the S curve typically announces a future infarct. This would be detected at a particular point in time. However, if it is not followed by further anomalies, it could simply be disregarded. This neuron can be trained to teach it normal associations between anomalies or expected consequences to a particular anomaly according to the known sicknesses.

The Scaling neuron for problematic amplitudes is used to determine personal thresholds for each patient. Since the system must be trained for each patient, some problems with the standard QRS curve must be identified. The standard QRS for a particular patient is first trained. The P and T curves are also trained. The scaling neuron then uses these data and compares them to a typically QRS, P and T curve which was determined in a laboratory. It then creates models which could correspond to problematic curves as a function of the normal curves. For example, if it is determined that an extra ventricular systole is detected by the substantial increase of the amplitude and the width of the QRS curve, the model will be extrapolated from the standard QRS curve for the patient and the laboratory standard and sick curve. A point-to-point diction algorithm is used to re-evaluate the distances and vector points using baselines such as x−1 or x/2. The models are then translated into tolerance models that can be used by the neural network.

Referring back to FIG. 9, when the Neural Network Base 244 detects any type of heart problem, the signal is sent to the compression module 250 and to a storage unit 253 for storage. The compression module 250 is used for better storage capacity. The storage unit 253 is used to define the storage structure. Preferably, only the data surrounding the occurrence of the trend are stored to reduce the memory required. Referring back to FIG. 7, the stored data is then sent to a locating module 112 using the emergency alarm transmitter 111. The neural network base 244 preferably triggers the cardiac anomaly detector 110 to manage the next actions. The locating module 112, which automatically takes the GPS positioning 221 of the patient every minute, tries to obtain the position again. If the last position is accurate, the system uses that location. If not, the positions of the patient in the last 10 minutes are retrieved to determine the person's movement or speed. With this data, a call is made to a central number by the emergency alarm transmitter 111 using the cellular module 224. The data about the anomaly is then sent with the personal ID of the person and an ECG monitor reading of his heart activity from the ECG data acquisition module 114. This alarm message is received by the health monitoring central station 113 and the person or computer in the central station can ask for further ECG data, for example for the last hour's ECG. The entire emergency call takes less than 6 seconds and is preferably fully automated, from the trigger of the call to the forwarding of any additional ECG or anomaly data required. A person having a heart attack only has four to eight minutes to obtain medical assistance. Most of the time, a person having a heart attack is unable to dial 911 or ask for assistance himself. That is why the automated call for help is very advantageous.

The personal information given by the device to the central station is preferably the name of the patient, his medical state and history, and the ECG signal and/or trend data. As soon as the location is found, this information is also transmitted to the Emergency Alarm Station.

Thereafter, once these data are sent, connection is established between ECG module and the cellular module to create a mini-center of telemedicine in order to be able to obtain the ECG curve of the remote patient. The whole process is carried out automatically.

The Health Monitoring Central Station 113 is an Emergency Station which, contrary to a typical 911 Emergency Station, does not require a voice call to obtain the person's status and location. It is a completely digitally-enabled station which allows a emergency clerk to talk to the patient through the speakers of the handheld device he is carrying but which does not require a response from the patient to send appropriate medical assistance to the exact position of the patient. The Station is able to receive the ECG signal and follow the state of the patient. It can then relay that information to the medical team who is assigned to the patient.

The digital emergency station 113 allows the reception and remote analysis of data received by the Cardiac data acquisition module. Be it directly by modem or via Internet, the system is able to physically locate the person on a map and to thus provide to the various technicians at the Station, the data necessary to find the person as well as a constant status report. Then, it is possible to follow the status of the person by telemetry throughout the search for the person or to communicate with her or the people around her via the cellular module provided with a loudspeaker and a hands free microphone. The whole process is made automatically and requires only a few seconds in total. A station can treat more than one request at the same time.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A trend detection method for detecting trends in an electrocardiogram monitoring signal of a patient, comprising:
    extracting locations of base points from said electrocardiogram monitoring signal;
    for each said location of base points, the location of the base point is compared against a predetermined threshold range based on a slow adaptative learning process using said patient's own cardiac movement, said range having an upper and lower threshold value for both an horizontal and vertical adjusted value for each of said base points;
    if all locations are within the predetermined, threshold range, performing a proximity analysis to determine improbable locations;
    if all locations are possible, determining an occurrence of a trend in said electrocardiogram monitoring signal from said locations.

2. A trend detection method as claimed in claim 1, further comprising providing a portable electrocardiogram monitor generating said electrocardiogram monitoring signal, wherein said portable electrocardiogram can be worn during day-to-day activities and for long periods.

3. A trend detection method as claimed in claim 1, further comprising extracting and storing trend data corresponding to said occurrence.

4. A trend detection method as claimed in claim 1, further comprising
    providing a relative position between two base points, which refers to a normal PQRST morphology learned from past normal cardiac movements of said patient;
    and wherein said determining comprises determining if a position of one of said base points with respect to another one of said base points matches said relative position using said locations;
    wherein said trend is detected if said position does not match said relative position over a predetermined period of time.

5. A trend detection method as claimed in claim 1, further comprising
    providing a distance tolerance;
    and wherein said determining comprises determining if a distance between one of said base points and another one of said base points is acceptable using said locations and said distance tolerance, based on possible rhythm changes;
    wherein said trend is detected if said distance is not acceptable over a predetermined period of time.

6. A trend detection method as claimed in claim 1, further comprising
    providing a base model for said locations of base points;
    and wherein said determining comprises determining if said locations correspond to said base model;
    wherein said trend is detected if said locations do not correspond to said base model over a predetermined period of time.

7. A trend detection method as claimed in claim 1, wherein said electrocardiogram monitoring signal is a digital signal.

8. A trend detection method as claimed in claim 1, further comprising sending an alarm message when said trend is determined to have occurred.

9. A trend detection method as claimed in claim 8, further comprising extracting and storing trend data corresponding to said occurrence and wherein said alarm message comprises said trend data.

10. A trend detection method as claimed in claim 8, wherein said alarm message comprises identification data for said patient.

11. A trend detection method as claimed in claim 8, further comprising determining a geographical location for said patient and wherein said alarm message comprises geographical location data for said patient.

12. A trend detection system for detecting trends in an electrocardiogram monitoring signal of a patient, comprising:
    a threshold determiner for determining a predetermined threshold range based on a slow adaptative learning process using said patient's own cardiac movement, said range having an upper and lower threshold value for both an horizontal and vertical adjusted value for modelized base points of said patient's own cardiac movement;
    a base point location extractor for extracting locations of current base points from said electrocardiogram monitoring signal;
    a threshold comparator for comparing each said location of current base points against said predetermined threshold range;
    a proximity analyzer for performing a proximity analysis if all current locations are within the predetermined threshold range to determine improbable locations;
    a trend occurrence determiner for determining an occurrence of a trend in said electrocardiogram monitoring signal from said current locations, if all locations are possible.

13. A trend detection system as claimed in claim 12, further comprising a portable electrocardiogram monitor generating said electrocardiogram monitoring signal wherein said portable electrocardiogram can be worn during day-to-day activities and for long periods.

14. A trend detection system as claimed in claim 12, further comprising a trend data extractor for extracting and storing trend data corresponding to said occurrence.

15. A trend detection system as claimed in claim 12, wherein said trend occurrence determiner determines if a position of one of said base points with respect to another one of said base points matches a relative position between two base points, which refers to a normal PQRST morphology learned from past normal cardiac movements of said patient using said locations;

wherein said trend is detected if said position does not match said relative position between two base points over a predetermined period of time.

16. A trend detection system as claimed in claim 12, wherein said trend occurrence determiner determines if a distance between one of said base points and another one of said base points is acceptable using said locations and a distance tolerance, based on possible rhythm changes;

wherein said trend is detected if said distance is not acceptable over a predetermined period of time.

17. A trend detection system as claimed in claim 12, wherein said trend occurrence determiner determines if said locations correspond to a base model for said locations of base points;

wherein said trend is detected if said locations does not correspond to said base model over a predetermined period of time.

18. A trend detection system as claimed in claim 12, wherein said electrocardiogram monitoring signal is a digital signal.

19. A trend detection system as claimed in claim 12, further comprising an alarm transmitter for sending an alarm message when said trend is determined to have occurred.

20. A trend detection system as claimed in claim 19, further comprising a trend data extractor for extracting and storing trend data corresponding to said occurrence and wherein said alarm message comprises said trend data.

21. A trend detection system as claimed in claim 19, wherein said alarm message comprises identification data for said patient.

22. A trend detection system as claimed in claim 19, further comprising a geographical location system for determining a geographical location for said patient and wherein said alarm message comprises geographical location data for said patient.

* * * * *